United States Patent
Wingen et al.

(10) Patent No.: US 6,403,172 B1
(45) Date of Patent: Jun. 11, 2002

(54) BENZOTHIOPHENES, AND THEIR USE IN LIQUID-CRYSTALLINE MIXTURES

(75) Inventors: Rainer Wingen, Hattersheim (DE); Ayako Ogawa, Kakegawa (JP); Barbara Hornung, Hasselroth; Wolfgang Schmidt, Köln, both of (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 09/532,699

(22) Filed: Mar. 22, 2000

(30) Foreign Application Priority Data

Mar. 24, 1999 (DE) .......................... 199 13 349

(51) Int. Cl.⁷ .................. C09K 19/32; C09K 19/34; C07D 333/52; C07D 333/72
(52) U.S. Cl. ............... 428/1.1; 252/299.61; 252/299.62; 549/49; 549/50; 549/51; 549/52
(58) Field of Search ................. 252/299.62, 299.61; 428/1.1; 549/32, 33, 49, 50, 51, 52

(56) References Cited

U.S. PATENT DOCUMENTS

| | | | | |
|---|---|---|---|---|
| 5,496,500 A | * | 3/1996 | Toyne et al. ........... | 252/299.61 |
| 6,008,377 A | * | 12/1999 | Jones et al. ................. | 549/51 |
| 6,020,531 A | * | 2/2000 | Shiraiwa et al. ............ | 568/425 |
| 6,096,781 A | * | 8/2000 | Cullinan ...................... | 514/438 |

FOREIGN PATENT DOCUMENTS

| | | | |
|---|---|---|---|
| CH | 559758 | * | 3/1975 |
| DE | 33 46 175 | | 7/1985 |
| DE | 196 30 068 | | 1/1998 |
| DE | 197 48 432 | | 5/1999 |
| EP | 0032362 | | 7/1981 |
| EP | 0364923 | | 4/1990 |
| EP | 0392510 | | 10/1990 |
| EP | 0459406 | | 12/1991 |
| EP | 0458347 | | 9/1996 |
| EP | 835872 | * | 4/1998 |

* cited by examiner

Primary Examiner—Shean C. Wu
(74) Attorney, Agent, or Firm—Frommer Lawrence & Haug LLP

(57) ABSTRACT

Benzothiophene derivatives of the formula (I) are used as components of liquid-crystal mixtures (I)

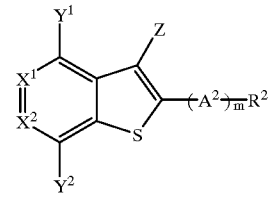

where the symbols and indices have the following meanings:

$X^1$ and $X^2$, independently of one another, are —CH—, —CF—, the —($R^1$)C— group or the —($R^1$—$A^1$—$M^1$)C— group, with the provisos that x1) $X^1$ and $X^2$ are not simultaneously the —($R^1$)C— or —($R^1$—$A^1$—$M^1$)C— group, and x2) $X^1$ and $X^2$ are only simultaneously —CH— or —CF— if Z is fluorine $Y^1$ and $Y^2$, independently of one another, are hydrogen or fluorine, but both are not simultaneously fluorine z is hydrogen or fluorine $R^1$ and $R^2$, independently of one another, are, for example, a straight-chain or branched alkyl radical (with or without asymmetrical carbon atoms) having 1 to 20 carbon atoms, $A^1$ and $A^2$ are, for example, phenylene-1,4-diyl, $M^1$ is undirected and is —OC(=O)—, —OC(=O)O—, —OCH$_2$—, —(CH$_2$)$_n$—, —OC(=O)CH$_2$CH$_2$—, —OCH$_2$CH$_2$CH$_2$—, —C≡C— or a single bond, m is 0 or 1, n is from 1 to 6.

11 Claims, No Drawings

BENZOTHIOPHENES, AND THEIR USE IN LIQUID-CRYSTALLINE MIXTURES

RELATED APPLICATIONS

This application claims priority under 35 U.S.C. § 119 to German application No. 199 13 349.2, filed Mar. 24, 1999.

STATEMENT REGARDING FEDERALLY SPONSORED RESEARCH OR DEVELOPMENT

Not applicable.

BACKGROUND OF THE INVENTION

1. Field of the Invention

This invention provides for benzothiophenes and their use in liquid-crystalline mixtures and the use of these mixtures in display devices.

2. Description of Related Art

Besides nematic and cholesteric liquid crystals, optically active, tilted, smectic (ferroelectric) liquid crystals have also recently been used in commercial display devices.

Clark and Lagerwall have been able to show that the use of ferroelectric liquid crystals (FLCs) in very thin cells results in opto-electrical switching or display elements which have response times which are faster by a factor of up to 1000 compared with conventional TN ("twisted nematic") cells (see, for example, EP-A 0 032 362). Owing to this and other favorable properties, for example the possibility of bistable switching and the fact that the contrast is virtually independent of the viewing angle, FLCs are basically highly suitable for areas of application such as computer displays.

For a more in-depth explanation of the technical requirements of FLCs, see European Patent Application 97118671.3 and DE-A 197 48 432.

Thiophene derivatives have already been described for use in liquid-crystal mixtures:
thiophene derivatives, for example, in DE-A 33 46 175, EP-A-0 458 347, EP-A-0 364 923, EP-A-0 392 510, EP-A-0 459 406,
derivatives of benzothiophene-2-carboxylic acid in DE-A 196 30 068.

Since the development, in particular of ferroelectric liquid-crystal mixtures, can in no way be regarded as complete, the manufacturers of displays are interested in a very wide variety of components for mixtures, partly because only the interaction of the liquid-crystalline mixtures with the individual components of the display device or of the cells (for example the alignment layer) allow conclusions to be drawn on the quality of the liquid crystalline mixtures too.

SUMMARY OF THE INVENTION

It has now been found that benzothiophenes of the formula (I), even when admixed in small amounts, have a favorable effect on the properties of liquid-crystal mixtures, in particular chiral smectic mixtures, for example regarding the dielectric anisotropy and/or the melting point, but also regarding the switching behavior.

BRIEF DESCRIPTION OF THE SEVERAL VIEWS OF THE DRAWING(S)

Not applicable.

DETAILED DESCRIPTION OF THE INVENTION

The invention relates to the use of benzothiophenes of the formula (I) as components of liquid-crystal mixtures

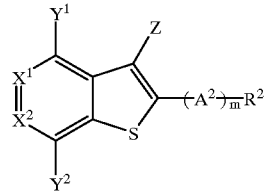

(I)

where the symbols and indices have the following meanings:
$X^1$ and $X^2$, independently of one another, are —CH—, —CF—, the —($R^1$)C— group or the —($R^1$—$A^1$—$M^1$)C— group, with the provisos that
x1) $X^1$ and $X^2$ are not simultaneously the —($R^1$)C— or —($R^1$—$A^1$—$M^1$)C— group, and
x2) $X^1$ and $X^2$ are only simultaneously —CH— or —CF— if Z is fluorine
$Y^1$ and $Y^2$, independently of one another, are hydrogen or fluorine, but both are not simultaneously fluorine
Z is hydrogen or fluorine
$R^1$ and $R^2$, independently of one another, are a straight-chain or branched alkyl radical (with or without asymmetrical carbon atoms) having 1 to 20 carbon atoms, where
a) one or two non-terminal —$CH_2$— groups may be replaced by —O— and/or —C(=O)— and/or —Si($CH_3$)$_2$—, with the proviso that two adjacent —$CH_2$— groups cannot be replaced by heteroatoms, and/or
b) one or more —$CH_2$— groups may be replaced by —CH=CH— and/or —C≡C—, and/or
c) one —$CH_2$— group may be replaced by cyclopropane-1,2-diyl, cyclobutane-1,3-diyl, cyclopentane-1,3-diyl, bicyclo-[1.1.1] pentane-1,3-diyl or cyclohexane-1,4-diyl, and/or
d) one or more H atoms may be replaced by F, and/or in the case of a branched alkyl radical containing asymmetrical carbon atoms, the asymmetrical carbon atoms either have —$CH_3$, —$OCH_3$, —$CF_3$, F, CN and/or Cl as substituents, or are incorporated into a 3-to 7-membered ring, in which, in addition, one or two non-adjacent —$CH_2$— groups may be replaced by —O— and one —$CH_2$— group may be replaced by —OC(=O)—
$A^1$ and $A^2$, independently of one another, are phenylene-1,4-diyl, unsubstituted, monosubstituted or disubstituted by CN or F, phenylene-1,3-diyl, unsubstituted, monosubstituted or disubstituted by CN or F, cyclohexane-1,4-diyl, in which one or two H atoms may be replaced by CN and/or $CH_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, 1,1'-biphenyl-4,4'-diyl, unsubstituted, monosubstituted or disubstituted by F, or 1,1'-phenylcyclohexyl-4,4'-diyl, in which the phenyl moiety is unsubstituted, monosubstituted or disubstituted by F
$M^1$ is undirected and is —OC(=O)—, —OC(=O)O—, —$OCH_2$—, —($CH_2$)$_n$—, —OC(=O)$CH_2CH_2$—, —$OCH_2CH_2CH_2$—, —C≡C— or a single bond
m is 0 or 1
n is from 1 to 6, i.e. 1, 2, 3, 4, 5 or 6.
Undirected is intended to mean that, in the case of asymmetrical groups, mirror and mirror image of the group can be employed.

The symbols and indices in the formula (I) preferably have the following meanings:

$R^1$ and $R^2$, independently of one another, are preferably a straight-chain or branched alkyl radical (with or without asymmetrical carbon atoms) having 2 to 18 carbon atoms, where a) one —$CH_2$— group may be replaced by —O—, and/or b) one or more H atoms may be replaced by F.

$R^1$ and $R^2$, independently of one another, are particularly preferably a straight-chain or branched alkyl radical (with or without asymmetrical carbon atoms) having 3 to 16 carbon atoms, where c) one —$CH_2$— group may be replaced by —O—.

$A^1$ and $A^2$, independently of one another, are preferably phenylene-1,4-diyl, phenylene-1,3-diyl, 1,1'-biphenyl-4,4'-diyl or 1,1'-phenyl-cyclohexyl-4,4'-diyl.

$A^1$ and $A^2$ are particularly preferably phenylene-1,4-diyl.

Z is preferably F, or

Z=H and $Y^1$=F or $Y^2$=F or $X^1$=—CF— or $X^2$=—CF—.

The following compounds of the formula (I-1) to (I-10) are particularly preferably employed:

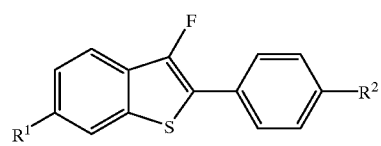

(I-1)

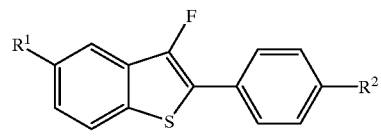

(I-2)

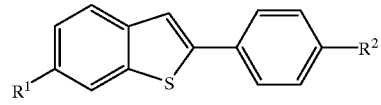

(I-3)

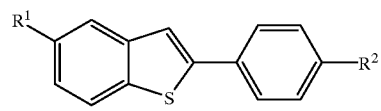

(I-4)

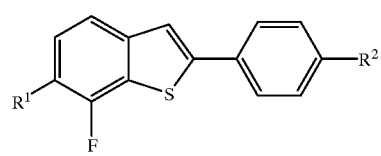

(I-5)

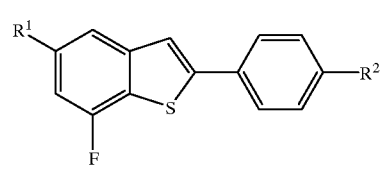

(I-6)

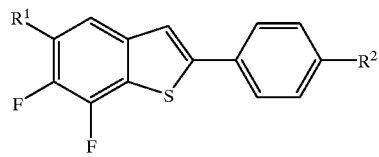

(I-7)

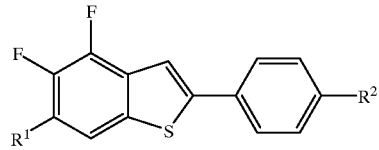

(I-8)

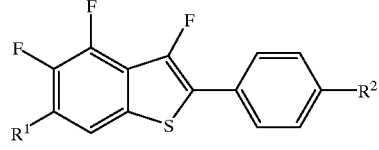

(I-9)

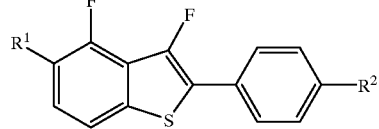

(I-10)

where $R^1$ and $R^2$ have the above-mentioned meanings and preferences.

The invention also relates to the benzothiophenes of the formula (I), as defined above.

The compounds according to the invention and employed according to the invention are prepared by methods known per se from the literature, as described in standard works on organic synthesis, for example Houben-Weyl, Methoden der Organischen Chemie [Methods of Organic Chemistry], Georg-Thieme-Verlag, Stuttgart.

However, it may prove necessary to vary or modify the literature methods for the requirements of mesogenic units, since, for example, functional derivatives having long (>C6) alkyl chains frequently have lower reactivity than, for example, the methyl and ethyl analogs.

Particular reference is made in this connection to the following references, which describe in general terms the synthesis of benzothiophene derivatives which are to be used, inter alia, as pharmaceuticals, but which do not reveal to the person skilled in the art the benzothiophenes according to the invention and their suitability as components of liquid-crystalline mixtures:

Reference 1:
Sauter et al., Monatshefte für Chemie 101, 1806–1816 (1970), for the preparation of 5-alkoxy-2-arylbenzothiophenes, which can also contain an additional carboxyl group in position 3.

Reference 2:
WO 97/34888 for the synthesis of 6-alkoxy-2-arylbenzothiophenes, which can also contain a bromine or carbonyl substituent in position 3.

Reference 3:
WO 96/02537 for the synthesis of 6-alkyl- or -alkoxybenzothiophenes, which can also contain a carbonyl substituent in position 3.

Reference 4:
U.S. Pat. No. 4,133,814 for the synthesis of 6-alkoxy-2-arylbenzothiophenes and a review of further routes to benzothiophenes.

Reference 5:
WO 97/01549 for the synthesis of 6-alkoxy-2-arylbenzothiophenes, which can also have a bromine or carbonyl substituent in position 3.

Reference 6:
EP-A-0 832 891 for the synthesis of fused aromatic compounds having a benzothiophene moiety and for further syntheses of 2-arylbenzothiophenes.

Reference 7:
Mol. Cryst. Liq. Cryst. (1978), 44(34), 193–5 [CAN 89:42642] and ibid., (1979), 54(3–4), 221–36 [CAN 93:7776], for the synthesis of mesogenic thiophenols.

Reference 8:
EP-A-0 439 170 for the synthesis of mesogenic phenacyl bromides.

Reference 9:
DE-A 44 20 926 for the synthesis of substituted benzothiophenes containing a carbonyl function in position 2.

Reference 10:
WO 98/03501 for the synthesis of 2,6-disubstituted benzothiophenes.

Reference 11:
WO 98/13363 for the synthesis of 6-alkoxy-3-aryl- and 6-alkoxy-2-arylbenzothiophenes.

Reference 12:
FR-A 2 752 840 for the synthesis of 2,3-substituted benzothiophenes containing a substituent in position 7 which is able to undergo halogen-metal exchange.

Reference 13:
EP-A-0 835 872 for the synthesis of 6-methyl-2-aryl-3-substituted benzothiophenes.

Reference 14:
EP-A-0 842 930 for the synthesis of 6-alkoxy-2—(4-alkoxyphenyl)benzothiophenes.

Reference 15:
WO 98/33793 for the synthesis of 7-bromo-3-methylbenzothiophene as precursor for more complex benzothiophenes.

Reference 16:
Tetrahedron Letters No. 37, pp. 4049–52, 1968, for the synthesis of polyfluorinated benzothiophenes.

Reference 17:
Tetrahedron Letters No. 17, pp. 2029–2032, 1968, for the synthesis of polyfluorinated benzothiophenes.

Reference 18:
J. Chem. Soc. Perkin Trans. I, 1973, 429–32, for the synthesis of polyfluorinated benzothiophenes.

Reference 19:
J. Chem. Soc. (C), 1968, 1225–37, for the synthesis of polyfluorinated benzothiophenes.

Reference 20:
J. Chem. Soc. (C), 1967, 865–73, for the synthesis of polyfluorinated benzothiophenes.

Reference 21:
EP-A-0 568 289 for the synthesis of functionalized benzothiophenes.

As far as the linking of functional derivatives of the benzothiophenes with other liquid-crystal-specific units is concerned, express reference is made to DE-A 197 48 432, which gives a list of methods customary to the person skilled in the art.

The invention also relates to the use of compounds of the above formula (I) in liquid-crystal mixtures, preferably smectic and nematic liquid-crystal mixtures, particularly preferably ferroelectric liquid-crystal mixtures. Particular preference is given to use in ferroelectric liquid-crystal mixtures operated in inverse mode or in displays having active matrix elements.

The invention furthermore relates to liquid-crystal mixtures, preferably smectic and nematic liquid-crystal mixtures, particularly preferably ferroelectric liquid-crystal mixtures, which comprise one or more compounds of the above formula (I).

The liquid-crystal mixtures according to the invention generally comprise from 2 to 35 components, preferably from 2 to 25 components, particularly preferably from 2 to 20 components.

They generally comprise from 0.01 to 80% by weight, preferably from 0.1 to 60% by weight, particularly preferably from 0.1 to 30% by weight, of one or more, preferably from 1 to 10, particularly preferably from 1 to 5, very particularly preferably from 1 to 3, compounds of the formula (I).

Further components of liquid-crystal mixtures which comprise compounds of the formula (I) are preferably selected from known compounds having smectic and/or nematic and/or cholesteric phases. Further mixture components which are suitable in this context are listed, in particular, in international patent application PCT/EP 96/03154 and DE-A 197 48 432, which are expressly incorporated herein by way of reference.

The mixtures according to the invention can in turn be used in electro-optical or fully optical elements, for example display elements, switching elements, light modulators, elements for image processing and/or signal processing, or generally in the area of nonlinear optics.

The invention furthermore relates to a switching or display device, preferably a device utilizing the smectic phases in the region of the working temperature. Particular preference is given to ferroelectric switching and/or display devices operated in normal or inverse ($\tau V_{min}$) mode (see, for example, J. C. Jones, M. J. Towler, J. R. Hughes, Displays 1993, 14, No. 2, 86–93; M. Koden, Ferroelectrics 1996, 179,121–129).

Particular preference is likewise given to ferroelectric switching and/or display devices containing active matrix elements (see, for example, DE-A 198 22 830).

The present application cites various documents, for example in order to illustrate the technical background to the invention. All these documents are expressly incorporated herein by way of reference.

The invention is explained in greater detail by the examples below without this being intended to represent a restriction thereto.

EXAMPLE 1

6-Hexyloxy-3-fluoro-2-(4-hexylphenyl)benzo [b] thiophene

6-Hexyloxy-2-(4-hexylphenyl)benzo[b]thiophene (obtained analogously to Reference 5 from 4-hexylphenacyl bromide [obtainable in accordance with Reference 8] and 3-hexyloxythiophenol [obtainable in accordance with Reference 7]) is converted into 3-bromo-6-hexyloxy-2-(4-hexylphenyl)benzo[b]thiophene analogously to Reference 5. 6-Hexyloxy-2-(4-hexylphenyl)benzo[b]thiophene-3-carboxylic acid is prepared therefrom analogously to Reference 2. The target compound is obtained therefrom by fluorodecarboxylation (see Forrest et al., Tetrahedron Lett., 36, 2117 (1995), or Wang et al., J. Chem. Soc., Chem. Commun. 2399 (1995)), using F-TEDA-BF$_4$ (see Banks, R. E., J. Fluorine Chem. (1998), 87(1), 1–17 [CAN 128:216948]).

The compounds of the formula (I) in which
$R^1$ in the —($R^1$)C— group is an alkyl or alkoxy radical having 1 to 20 carbon atoms, and $R^2$ is an alkyl or alkoxy radical having 1 to 20 carbon atoms can be obtained analogously

EXAMPLE 2

7-Fluoro-2-(4-hexylphenyl)-5-octyloxybenzo[b]thiophene is obtained by reacting 3-fluoro-4-methoxythiophenol (obtainable analogously to Reference 7 from 3-fluoro-4-methoxyaniline [366-99-4]) and 4-hexylphenacyl bromide analogously to Reference 5 to give 7-fluoro-2-(4-hexylphenyl)-5-methoxybenzo[b]thiophene, ether cleavage by means of hydrobromic acid/acetic acid to give 7-fluoro-2-(4-hexylphenyl]-5-hydroxybenzo[b]thiophene and Williamson ether synthesis using octyl bromide in 2-butanone in the presence of potassium carbonate.

The compounds of the formula (I) in which a) $R^1$ in the —$(R^1)C$— group is an alkyl, alkoxy or alkylcarbonyloxy radical having 1 to 20 carbon atoms
$R^2$ is an alkyl or alkoxy radical having 1 to 20 carbon atoms b) $R^1$ in the —$(R^1—A^1—M^1)C$— group is an alkyl or alkoxy radical having 1 to 20 carbon atoms
$R^2$ is an alkyl or alkoxy radical having 1 to 20 carbon atoms $M^1$ is —C(=O)O—, —CH$_2$O—, —CH$_2$CH$_2$C(=O)O— or —(CH$_2$)$_3$O— can be obtained analogously.

EXAMPLE 3

6,7-Difluoro-2-(4-hexylphenyl)-5-heptyloxybenzo[b]thiophene is obtained by reacting 2,3-difluoro-4-ethoxythiophenol (obtainable analogously to Reference 7 from 2,3-difluoro-4-ethoxyaniline [189751-13-1]) and 4-hexylphenacyl bromide analogously to Reference 5 to give 6,7-difluoro-2-(4-hexylphenyl)-5-ethoxybenzo[b]thiophene, ether cleavage by means of hydrobromic acid/acetic acid to give 6,7-difluoro-2-(4-hexylphenyl)-5-hydroxybenzo[b]thiophene and Williamson ether synthesis using heptyl bromide in 2-butanone in the presence of potassium carbonate.

The compounds of the formula (I) in which a) $R^1$ in the —$(R^1)C$— group is an alkyl, alkoxy or alkylcarbonyloxy radical having 1 to 20 carbon atoms
$R^2$ is an alkyl or alkoxy radical having 1 to 20 carbon atoms b) $R^1$ in the —$(R^1—A^1—M^1)C$— group is an alkyl or alkoxy radical having 1 to 20 carbon atoms $R^2$ is an alkyl or alkoxy radical having 1 to 20 carbon atoms $M^1$ is —C(=O)O—, —CH$_2$O—, —CH$_2$CH$_2$C(=O)O— or —(CH$_2$)$_3$O—can be obtained analogously.

EXAMPLE 4

6,7-Difluoro-2-(4-hexylphenyl)-5-octylbenzo[b]thiophene is obtained analogously to Example 3, but the hydroxyl compound is converted into the corresponding triflate, and the latter is converted into the target compound by means of the 9-BBN adduct of oct-1-ene with Pd catalysis.

The compounds of the formula (I) in which a) $R^1$ in the —$(R^1)C$— group is an alkyl radical having 1 to 20 carbon atoms $R^2$ is an alkyl or alkoxy radical having 1 to 20 carbon atoms b) $R^1$ in the —$(R^1—A^1—M^1)C$— group is an alkyl or alkoxy radical having 1 to 20 carbon atoms $R^2$ is an alkyl or alkoxy radical having 1 to 20 carbon atoms $M^1$ is a single bond can be obtained analogously.

EXAMPLE 5

2-(4-Hexylphenyl)-6-octyloxybenzo[b]thiophene is prepared analogously to Reference 14 (p. 16) from 6-methoxybenzo[b]thiophene-2-boronic acid and 4-hexylbromobenzene in a Suzuki reaction. The 2-(4-hexylphenyl)-6-methoxybenzo[b]thiophene obtained as the primary product is subjected to ether cleavage by means of hydrobromic acid/glacial acetic acid. The resultant hydroxyl compound gives the target compound in a Williamson ether synthesis using octyl bromide in 2-butanone in the presence of potassium carbonate.

The compounds of the formula (I) in which $R^1$ in the —$(R^1)C$— group is an alkoxy radical having 1 to 20 carbon atoms $R^2$ is an alkyl or alkoxy radical having 1 to 20 carbon atoms can be obtained analogously.

EXAMPLE 6

2-(4-Hexylphenyl)-6-octylbenzo[b]thiophene is prepared analogously to Example 5, but with the hydroxyl compound being converted further into the target compound analogously to Example 4.

The compounds of the formula (I) in which $R^1$ in the —$(R^1)C$— group is an alkyl radical having 1 to 20 carbon atoms $R^2$ is an alkyl or alkoxy radical having 1 to 20 carbon atoms can be obtained analogously.

What is claimed is:

1. A liquid-crystal mixture comprising at least one benzothiophene derivative of the formula (I)

(I)

where the symbols and indices have the following meanings:

$X^1$ and $X^2$, independently of one another, are —CH—, —CF—, the —$(R^1)C$— group or the —$(R^1—A^1—M^1)C$— group, with the provisos that x1) $X^1$ and $X^2$ are not simultaneously the —$(R^1)C$— or —$(R^1—A^1—M^1)C$— group, and x2) $X^1$ and $X^2$ are only simultaneously —CH— or —CF— if Z is fluorine $Y^1$ and $Y^2$, independently of one another, are hydrogen or fluorine, but both are not simultaneously fluorine Z is hydrogen or fluorine $R^1$ and $R^2$, independently of one another, are a straight-chain or branched alkyl radical (with or without asymmetrical carbon atoms) having 1 to 20 carbon atoms, where a) one or two non-terminal —CH$_2$— groups may be replaced by —O— and/or —C(=O)— and/or —Si(CH$_3$)$_2$—, with the proviso that two adjacent —CH$_2$— groups cannot be replaced by heteroatoms, and/or b) one or more —CH$_2$— groups may be replaced by —CH=CH— and/or —C≡C—, and/or c) one —CH$_2$— group may be replaced by cyclopropane-1,2-diyl, cyclobutane-1,3-diyl, cyclopentane-1,3-diyl, bi-cyclo[1.1.1]pentane-1,3-diyl or cyclohexane-1,4-diyl, and/or
d) one or more H atoms may be replaced by F, and/or
e) in the case of a branched alkyl radical containing asymmetrical carbon atoms, the asymmetrical carbon atoms either
have —CH$_3$, —OCH$_3$, —CF$_3$, F, CN and/or Cl as substituents, or
are incorporated into a 3- to 7-membered ring, in which, in addition, one or two non-adjacent —CH$_2$— groups may be replaced by —O— and one —CH$_2$— group may be replaced by —OC(=O)—

A$^1$ and A$^2$, independently of one another, are phenylene-1,4-diyl, unsubstituted, monosubstituted or disubstituted by CN or F, phenylene-1,3-diyl, unsubstituted, monosubstituted or disubstituted by CN or F, cyclohexane-1,4-diyl, in which one or two H atoms may be replaced by CN and/or CH$_3$ and/or F, 1-cyclohexene-1,4-diyl, in which one H atom may be replaced by F, 1-alkyl-1-silacyclohexane-1,4-diyl, pyridine-2,5-diyl, unsubstituted or monosubstituted by F, pyrimidine-2,5-diyl, unsubstituted or monosubstituted by F, 1,1'-biphenyl-4,4'-diyl, unsubstituted, monosubstituted or disubstituted by F, or 1,1'-phenylcyclohexyl-4,4'-diyl, in which the phenyl moiety is unsubstituted, monosubstituted or disubstituted by F M$^1$ is undirected and is —OC(=O)—, —OC(=O)O—, —OCH$_2$—, —(CH$_2$)$_n$—, —OC(=O)CH$_2$CH$_2$—, —OCH$_2$CH$_2$CH$_2$—, —C≡C— or a single bond m is 0 or 1 n is from 1 to 6.

2. A liquid-crystal mixture as claimed in claim 1, in which, in the compound of the formula (I), R$^1$ and R$^2$, independently of one another, are a straight-chain or branched alkyl radical (with or without asymmetrical carbon atoms) having 2 to 18 carbon atoms, where
a) one —CH$_2$— group may be replaced by —O—, and/or
b) one or more H atoms may be replaced by F.

3. A liquid-crystal mixture as claimed in claim 1, wherein, in the compounds of the formula (I), A$^1$ and A$^2$, independently of one another, are phenylene-1,4-diyl, phenylene-1,3-diyl, 1,1'-biphenyl-4,4'-diyl or 1,1'-phenyl-cyclohexyl-4,4'-diyl.

4. A liquid-crystal mixture as claimed in claim 1, wherein, in the compounds of the formula (I), Z is hydrogen and Y$^1$=F or Y$^2$=F or X$^1$=—CF— or X$^2$=—CF—.

5. A liquid-crystal mixture as claimed in claim 1, which comprises from 0.01 to 80% by weight of one or more compounds of the formula (I).

6. A liquid-crystal mixture as claimed in claim 1, which is ferroelectric (chiral smectic).

7. A liquid-crystal mixture as claimed in claim 1, which is nematic.

8. A ferroelectric switching or display device containing a ferroelectric liquid-crystal mixture as claimed in claim 1.

9. A ferroelectric switching or display device as claimed in claim 8, which is operated in $\tau V_{(min)}$ mode.

10. A ferroelectric switching or display device as claimed in claim 8, which contains active matrix elements.

11. A benzothiophene of the formula (I)

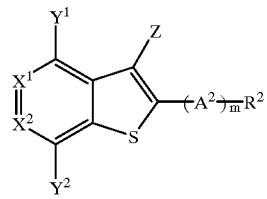

(I)

where the symbols and indices have the following meanings:
X$^1$ and X$^2$, independently of one another, are —CH—, —CF—, the —(R$^1$)C— group or the —(R$^1$—A$^1$—M$^1$)C—group, with the provisos that
x1) X$^1$ and X$^2$ are not simultaneously the —(R$^1$)C— or —(R$^1$—A$^1$—M$^1$)C— group, and
x2) X$^1$ and X$^2$ are only simultaneously —CH— or —CF— if Z is fluorine Y$^1$ and Y$^2$, independently or one another, are hydrogen or fluorine, but both are not simultaneously fluorine Z is hydrogen or fluorine R$^1$ and R$^2$, independently of one another, are a straight-chain or branched alkyl radical (with or without asymmetrical carbon atoms) having 2 to 18 carbon atom, where
(a) one or two non-terminal —CH$_2$— groups may be replaced by —C(=O)— and/or —Si(CH$_3$)$_2$—, and/or in the case of R$^1$ also by —O—, with the proviso that two adjacent —CH$_2$— groups cannot be replaced by heteroatoms, and/or
(b) one or more —CH$_2$— groups may be replaced by —CH=CH— and/or —C≡C—, and/or
(c) one —CH$_2$— group may be replaced by cyclopropane-1,2-diyl, cyclobutane-1,3-diyl, cyclopentane-1,3-diyl, bi-cyclo[1.1.1]pentane-1,3-diyl or cyclohexane- 1,4-diyl, and/or
(d) one or more H atoms may be replaced by F, and/or
(e) in the case of a branched alkyl radical containing asymmetrical carbon atoms, the asymmetrical carbon atoms either
have —CH$_3$, —OCH$_3$, —CF$_3$, F, CN and/or Cl as substituents, or
are incorporated into a 3-to 7-membered ring, in which, in addition, one or two non-adjacent —CH$_2$— groups may be replaced by —O— and one —CH$_2$— group may be replaced by —OC(=O)—

A$^1$ and A$^2$, independently of one another, are phenylene-1,4-diyl, unsubstituted, monosubstituted or disubstituted by CN or F, phenylene-1,3-diyl, unsubstituted, monosubstituted or disubstituted by CN or F, 1-alkyl-1-silacyclohexane-1,4-diyl, pyridine-2,5-diyl, unsubstituted or monosubstituted by F, pyrimidine-2,5-diyl, unsubstituted or monosubstituted by F, pyrimidine-2,5-diyl, unsubstituted or monosubstituted by F, 1,1'-phenylcyclohexyl-4,4'-diyl, in which the phenyl moiety is unsubstituted, monosubstituted or disubstituted by F M$^1$ is undirected and is —OC(=O)—, —OC(=O)O—, —OCH$_2$—, (CH$_2$)$_n$—, —OC(=O)CH$_2$CH$_2$—, —OCH$_2$CH$_2$CH$_2$—, —C≡C— or a single bond m is 1 n is from 1 to 6.

* * * * *